(12) United States Patent
Hawkins et al.

(10) Patent No.: US 7,645,883 B1
(45) Date of Patent: *Jan. 12, 2010

(54) ENERGETIC IONIC LIQUIDS

(75) Inventors: Tom W. Hawkins, Lancaster, CA (US); Gregory W. Drake, Madison, AL (US); Adam J. Brand, Palmdale, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 565 days.

This patent is subject to a terminal disclaimer.

(21) Appl. No.: 11/398,746

(22) Filed: Mar. 30, 2006

(51) Int. Cl.
*C07D 257/00* (2006.01)
(52) U.S. Cl. ..................................................... 548/255
(58) Field of Classification Search .................. 548/255
See application file for complete search history.

(56) References Cited

U.S. PATENT DOCUMENTS 6,509,473 B1 * 1/2003 Drake ....................... 548/262.2
7,550,601 B1 * 6/2009 Drake et al. ................ 548/255

OTHER PUBLICATIONS

U.S. Appl. No. 11/203,578, filed Aug. 15, 2008 no pg pub number available.*

* cited by examiner

*Primary Examiner*—Golam M. M. Shameem
*Assistant Examiner*—Susannah Chung
(74) *Attorney, Agent, or Firm*—AFMCLO/JAZ; Thomas C. Stover

(57) ABSTRACT

Provided is a TNT replacement comprising one or more ionic liquids selected from the group of a triazolium salt, substituted triazolium salt and mixtures thereof.

7 Claims, No Drawings

ENERGETIC IONIC LIQUIDS

STATEMENT OF GOVERNMENT INTEREST

The invention described herein may be manufactured and used by or for the Government for governmental purposes without the payment of any royalty thereon.

CROSS REFERENCE TO RELATED PATENT APPLICATIONS

This application relates to U.S. patent application Ser. No. 11/203,578, by Drake et al, which relates to triazolium salts.

FIELD OF THE INVENTION

This invention relates to TNT replacements for use in explosives, particularly energetic ionic liquids.

BACKGROUND OF THE INVENTION

The costs of complying with environmental regulations led to a loss of domestically produced 2,4,6-trinitrotoluene (TNT) for use in melt-castable explosives. In addition, TNT has been the current state-of-the-art in melt-cast explosives.

However, the vapor toxicity of TNT can require protective measures in processing techniques in order to ensure employee safety. In addition, the toxic by-product (sulfated nitrotoluene) produced during manufacturing known as "red water", has incurred great cost associated with processing the production waste stream. Although a "greener" process is being developed in this country, the replacement of TNT with a low melting energetic salt offers several advantages. Energetic salts have the potential for improved explosive performance, higher density, negligible vapor pressure, and in some cases lower shock sensitivity.

Related is U.S. Pat. No. 6,509,473 to Drake (2003), which refers to triazolium salts but not as TNT replacements. Accordingly, there is need and market for one or more TNT replacements to overcome the above prior art shortcomings.

There has now been developed such TNT replacements which permit safer processing techniques and serve as effective substitutes for TNT for use in melt-castable explosives.

SUMMARY OF THE INVENTION

Broadly, the present invention provides a TNT replacement prepared from one or more ionic liquids. Such ionic liquids include a triazolium salt, substituted triazolium salt and/or mixtures thereof.

The invention also provides a TNT replacement comprising one or more triazolium salts selected from the group of 4-amino-1,2,4-triazolium perchlorate (4-ATP), 4-amino-1,2,4-triazolium nitrate (4-ATN), 1-H-1,2,4,-triazolium perchlorate (TP), 1-amino-3-methyl-1,2,3-triazolium nitrate (1-AMTN) and 1-methyl-4-amino-1,2,4-triazolium perchlorate (MATP).

The invention further provides a TNT replacement comprising an ionic liquid selected from the group of 4-ATP, 4-ATN, TP and eutectic mixtures thereof as well as 1-AMTN and MATP.

Thus the present invention focuses on synthesizing ionic liquids in the form of triazolium-based salts that have the appropriate physical and safety properties, thermal stability and performance to replace TNT, for use in melt-castable explosives.

DEFINITIONS

By "ionic liquids", as used herein, is meant salts that exist in the liquid state at or below the boiling point of water (100° C.).

That is, ionic liquids have essentially no vapor pressure and therefore negligible vapor toxicity in the liquid state. As a lower toxicity replacement for TNT, operational costs and risks can be lowered.

DESCRIPTION OF PREFERRED EMBODIMENTS

Suitable triazolium salts with utility as melt castable explosives include the nitrate, perchlorate, and dinitramide salts of 1-H-1,2,4-triazole, 1-R-4-amino-1,2,4 triazole (where R=H, $NH_2$, $N_2H_3$, $HONH_1$, $CH_3$, $C_2H_5$, $C_2H_4OH$, CN, or $CH_2CN$), 1-amino-3-R-1,2,3-triazole (where R=H, $NH_2$, $N_2H_3$, $HONH_1$, $CH_3$, $C_2H_5$, $C_2H_4OH$, CN, or $CH_2CN$), 1-H-1,2,3 triazole, and 3,4,5-triamino-1,2,4-triazole.

The formulas of certain of such triazoles are as shown below:

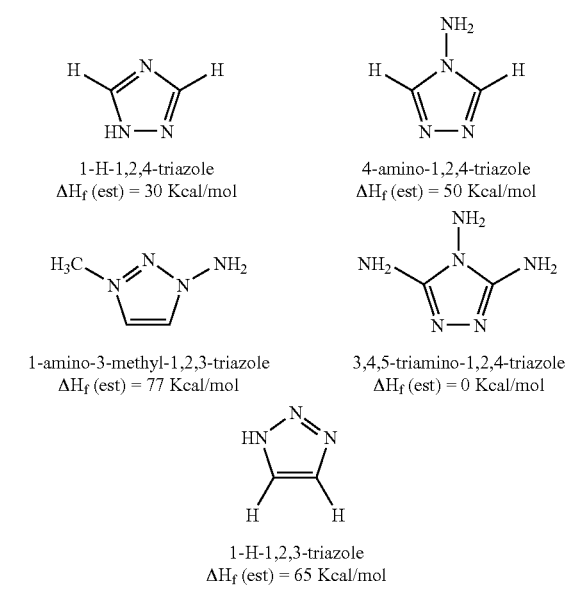

1-H-1,2,4-triazole
$\Delta H_f$ (est) = 30 Kcal/mol 4-amino-1,2,4-triazole
$\Delta H_f$ (est) = 50 Kcal/mol 1-amino-3-methyl-1,2,3-triazole
$\Delta H_f$ (est) = 77 Kcal/mol 3,4,5-triamino-1,2,4-triazole
$\Delta H_f$ (est) = 0 Kcal/mol 1-H-1,2,3-triazole
$\Delta H_f$ (est) = 65 Kcal/mol Accordingly, a type of melt castable explosive consisting of a triazolium salt, substituted triazolium salt, and/or mixture thereof is envisioned. Triazolium salt-based melt castable explosives may include eutectic or near eutectic mixtures of triazolium salts along with other explosive or oxidizing salts. Minor ingredients may also be incorporated which can include stabilizing or desensitizing additives such as wax. This type of explosive composition is capable of attaining superior explosive performance (detonation energy, shock pressure, detonation velocity, etc) and a similar processing temperature to TNT.

Thus, examples of single salts, binary eutectic mixtures, and explosive formulations are given as follows: The salts 4-amino-1,2,4-triazolium perchlorate (4-ATP) and 1-amino-3-methyl-1,2,3-triazolium nitrate (1-AMTN) have melt points of 84° C. and 88° C. respectively, allowing them to be readily castable at moderate processing temperatures. Additionally, mixtures of 4-ATP with 4-amino-1,2,4-triazolium nitrate (4-ATN) or 1-H-1,2,4,-triazolium perchlorate (TP)

form eutectic compositions with melt points approaching 70° C. Traditional explosive compounds may be incorporated to further enhance the explosive performance of these salts to create formulations that are analogous to current TNT-based formulations such as Comp B, Amatol, Tritonal, Torpex, etc. Other traditional energetic ingredients can include RDX, HMX, CL-20, PETN, nitroguanidine (NQ), and/or oxidizing salts such as ammonium perchlorate (AP), ammonium nitrate (AN), lithium nitrate (LiN), or lithium perchlorate (LiP).

The formulas of certain of the above triazolium salts are presented below:

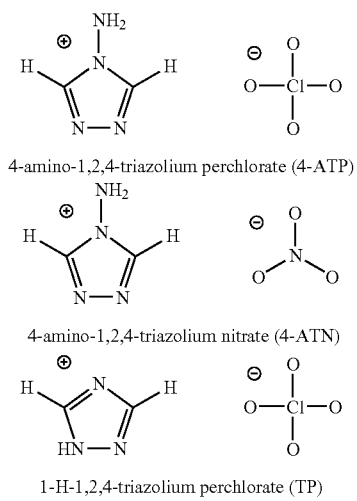

4-amino-1,2,4-triazolium perchlorate (4-ATP)

4-amino-1,2,4-triazolium nitrate (4-ATN)

1-H-1,2,4-triazolium perchlorate (TP)

Further, a new family of energetic ionic liquids based on the 1-amino-3-alkyl-1,2,3-triazolium heterocycle was synthesized at AFRL. One of the salts with a short alkyl group, 1-amino-3-methyl-1,2,3-triazole nitrate (1-AMTN), was identified as a viable candidate as a TNT replacement due to its relatively high melt point of 88° C. The ensuing chemical and physical properties characterization of 1-AMTN has yielded encouraging results. The properties listed for 1-AMTN far exceed the desired threshold values chosen for initial screening in contrast to the unsubstituted 1,2,3-triazolium family of salts which was eliminated from further investigation due to either unacceptable thermal stability or impact sensitivity values. The amino and alkyl group addition to the heterocycle appear to offer significant improvement in the molecular stability.

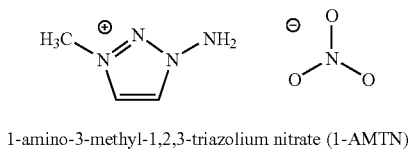

1-amino-3-methyl-1,2,3-triazolium nitrate (1-AMTN)

A further promising ionic liquid and triazolium salt was found to be 1-methyl-4-amino-1,2,4-triazolim perchlorate (MATP). Current research efforts indicate this molecule possesses a melting point almost identical to TNT, and the IL's high heat of formation and better oxygen balance should lend improved performance properties. The alkylation of the cation will also act to improve stability. Table 1 shows MATP to have better demonstrated performance with regards to shock velocity than TNT.

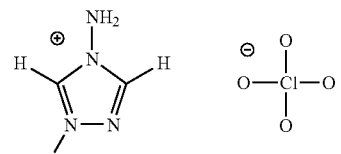

1-methyl-4-amino-1,2,4-triazolium perchlorate (MATP)

The synthesis of several of the triazolium salts (4-ATP, 4-ATN & TP) was carried out by neutralization of commercially available triazoles dissolved in methanol with concentrated nitric and perchloric acids. The salts were crystallized out of solution with ether and dried under vacuum. Ultimately, the synthesis of several 50 gram batches of the above mentioned materials were required to perform a rate stick test and to support the eutectic mixture effort.

A great deal of effort was dedicated to the synthesis of 1-AMTN due to the fact that the starting heterocycle is not commercially available. The making of the 1-amino-3-methyl-1,2,3-triazole cation is a two step process involving the cyclization of glyoxal bishydrazone. The addition of the alkyl group was accomplished by reacting the 1-amino-1,2,3-triazole with excess methyliodide in acetonitrile. The iodide salt was then converted to the nitrate salt by adding silver nitrate, resulting in a 4 step synthesis.

The synthesis of MATP at the gram scale was repeated to confirm previously obtained physical properties as well as provide material for additional small scale tests such as vacuum thermal stability. The preparation of MATP is similar to that of 1-AMTN, but is only a two step process due to the commercial availability of 4-amino-1,2,4-triazole starting material. However, the synthesis, at least currently, still requires the use of silver ($AgClO_4$) for the metathesis with the triazolium iodide salt.

Certain physical properties of the above-selected triazolium salts are given below in Table 1.

TABLE 1

Properties of Triazolium Salts

| Molecule | Melt Point (° C.) | Density (g/cc) | $V^*_{det}$ (km/s) | VTS (cc gas/g @ STP for 48 hrs at 100° C.) | Impact Sensitivity (Kg-cm) |
|---|---|---|---|---|---|
| TNT | 81 | 1.65 | 6.9* (6.3)** | <.01 | >200 |
| 4-ATP | 84 | 1.82 | 8.3 | .10 | 30 |
| MATP | 85 | 1.62 | 7.3 | <.01 | 80 |
| 1-AMTN | 88 | 1.63 | 8.1 (theor.) | .04 | >200 |
| ATP/TP (70/30 Wt. %) | 67 | 1.80 | 8.5 (theor.) | Not tested | 32 |
| ATP/ATN (30/70 Wt. %) | 66 | — | 8.0 (theor.) | Not tested | >200 |

*Dobratz, B. M., "LLNL Explosives Handbook, Properties of Chemical Explosives and Explosive Simulants", Lawrence Livermore National Laboratory, Livermore, CA, UCRL-52997, Mar. 16, 1981.
**Measured at AFRL with melt-cast TNT at 90% TMD.

Thus, several families of triazolium-based energetic ionic liquids synthesized at AFRL have been assessed as potential TNT replacements in melt cast applications as either a single salt or in a binary eutectic mixture. 1-AMTN and MATP exhibit properties that demonstrated the feasibility of replacing TNT with an ionic liquid. Both salts easily passed accepted thermal stability tests, have appropriate melt points (85-88° C.), and have superior calculated performance over TNT. The theoretical performance of MATP was realized in a rate stick test which determined the shock velocity (a key indicator of explosive performance) to be 7.3 km/s versus 6.3 km/s achieved with TNT under the same test conditions. The theoretical performance of 4-ATP was also realized in a rate stick test which determined the shock velocity (key indicator of explosive performance) to be 8.3 km/s versus 6.3 km/s achieved with TNT under the same test conditions. These tests validated the potential performance advantage afforded by ionic liquids.

Thus, the invention provides a number of acceptable replacements for TNT, which have negligible vapor pressure and lend themselves to safer processing techniques. Thus it is desirable to have a melt castable explosive that has a low vapor pressure (low inhalation toxicity), "greener" synthesis, and higher explosive performance than TNT. The triazole-based salts described in this disclosure have negligible vapor pressures, have simple synthetic routes from commercially available starting materials, and have demonstrated superior performance.

Accordingly, new families of triazolium and substituted triazolium salts produced and characterized herein, have demonstrated attractive properties making them replacements for TNT, the state-of-the-art energetic material used in melt-cast explosive formulations. Substituted triazolium salts and eutectic mixtures with other triazolium salts and/or other explosive compounds have been identified that have a melt point between 70-100° C., a desirable range for melt-cast explosive processing. The use of a low melting salt to replace TNT offers the potential for superior explosive performance, higher density, lower shock sensitivity, and negligible vapor pressure. Several salts identified above have similar melt points to TNT and measured detonation shock velocities exceeding that of TNT.

Returning to 1-AMTN, it possesses excellent small-scale safety and thermal stability properties while still capable of surpassing TNT with respect to explosive performance due to its high heat of formation. This salt has also been found to be compatible with typical explosive ingredients. A ¾ inch diameter confined rate stick test was performed to measure the shock velocity. However, at that diameter 1-AMTN melt-cast @ 96% of theoretical maximum density (TMD) did not sustain a detonation. This indicates the significant shock insensitivity exhibited by 1-AMTN offers potential for insensitive munitions applications. The improved safety of handling, processing, transportation, and storage of explosive munitions containing this compound can well translate into lower costs.

Thus, a low melting triazolium or substituted triazolium salt has potential as a replacement for TNT in melt castable explosives. Commercial applications include primary, booster, and main charge explosives. The above salts offer the potential for improved explosive performance, higher density, lower shock sensitivity, and a negligible vapor pressure.

What is claimed is:

1. An ionic liquid composition comprising, a eutectic mixture of a plurality of triazolium salts selected from the group consisting of 4-amino-1,2,4-triazolium perchlorate (4-ATP), 4-amino-1,2,4-triazolium nitrate (4-ATN), 1-H-1,2,4,-triazolium perchlorate (TP), 1-amino-3-methyl-1,2,3-triazolium nitrate (1-AMTN) and 1-methyl-4-amino-1,2,4-triazolium perchlorate (MATP).

2. The ionic liquid composition of claim 1 comprising one or more triazolium salts selected from the group consisting of 4-ATP, 4-ATN, TP and eutectic or near eutectic mixtures thereof, 1-AMTN and MATP.

3. The ionic liquid composition of claim 2 having by weight eutectic mixtures of 4-ATP/4-ATN (70/30), 4-ATP/4-ATN (30/70), and 4-ATP/TP (30170).

4. The ionic liquid composition of claim 2 employed in melt castable applications as a single salt or in a binary eutectic mixture.

5. The ionic liquid composition of claim 2 employed in melt castable explosives comprising the nitrate, perchlorate and dinitramide salts of 1-H-1,2,4-triazole, 1-R-4-amino-1,2,4 triazole (where R=H, $NH_2$, $NH_2$, $HONH_1$, $CH_3$, $C_2H_5$, $C_2H_4OH$, CN, or $CH_2CN$), 1-amino-3-R-1,2,3-triazole (where R=H, $NH_2$, $N_2H_3$, $HONH_1$, $CH_3$, $C_2H_5$, $C_2H_4OH$, CN, or $CH_2CN$), and 3,4,5-triamino-1,2,4-triazole.

6. The ionic liquid composition of claim 2 having additives thereto selected from the group consisting of water as a melting point depressant and wax as a stabilizing or desensitizing additive.

7. The jonic liquid composition of claim 1 employed in melt castable explosives for a primary, booster or as main charge explosives.

* * * * *